United States Patent [19]

Arlt et al.

[11] 4,159,324

[45] Jun. 26, 1979

[54] COMBATING INSECTS, ACARIDS AND NEMATODES WITH O-(1-FLUORO-2-HALO-ETHYL)(THIONO)-PHOSPHORIC(PHOSPHONIC) ACID ESTER-AMIDES

[75] Inventors: Dieter Arlt, Cologne; Hellmut Hoffmann, Wuppertal; Bernhard Homeyer, Leverkusen; Wolfgang Behrenz, Overath; Ingeborg Hammann, Cologne, all of Fed. Rep. of Germany

[73] Assignee: Bayer Aktiengesellschaft, Leverkusen, Fed. Rep. of Germany

[21] Appl. No.: 806,888

[22] Filed: Jun. 15, 1977

[30] Foreign Application Priority Data

Jun. 29, 1976 [DE] Fed. Rep. of Germany ....... 2629016
Mar. 5, 1977 [DE] Fed. Rep. of Germany ....... 2709617

[51] Int. Cl.² .......................... A01N 9/36; C07F 9/24; C07F 9/65
[52] U.S. Cl. .............................. 424/220; 260/326.61; 260/959; 424/200; 544/157; 546/21
[58] Field of Search .......................... 260/959, 326.61; 424/220, 200; 544/157; 546/21

[56] References Cited

U.S. PATENT DOCUMENTS 2,947,773  8/1960  Allen .................................... 260/959
3,087,955  4/1963  Brust .................................. 260/959 X Primary Examiner—Anton H. Sutto Attorney, Agent, or Firm—Sprung, Felfe, Horn, Lynch & Kramer

[57] ABSTRACT

O-(1-Fluoro-2-halo-ethyl)(thiono)phosphoric(phosphonic) acid ester-amides of the formula

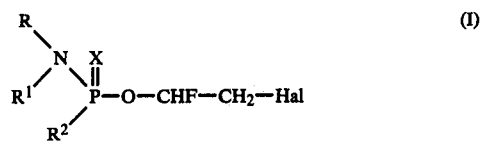

in which
R and $R^1$ independently represent hydrogen, alkyl, haloalkyl or cyanoalkyl, or
R and $R^1$ conjointly with the nitrogen atom form a heterocyclic ring which can optionally be interrupted by further hetero-atoms,
$R^2$ represents

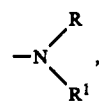

alkoxy, halogenalkoxy or alkyl,
Hal represents chlorine or bromine, and
X represents oxygen or sulphur, which possess insecticidal acaricidal and nematocidal properties.

10 Claims, No Drawings

COMBATING INSECTS, ACARIDS AND NEMATODES WITH O-(1-FLUORO-2-HALO-ETHYL)(THIONO)PHOSPHORIC(PHOSPHONIC) ACID ESTER-AMIDES

The present invention relates to and has for its objects the provision of particular new O-(1-fluoro-2-halo-ethyl)-thiono)phosphoric(phosphoic) acid ester-amides which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from U.S. Pat. Nos. 2,701,225, 2,947,773 and 3,453,348 that chlorine-substituted alkyl-phosphoric(phosphonic) acid esters, for example O,O-diethyl-O-(dichloroethyl)-phosphoric acid ester (Compound A) and O,O-di-methyl-2,2,2-trichloro-1-hydroxyethyl-phosphonic acid ester (Compound B), are distinguished by an insecticidal and acaricidal activity.

The present invention provides new O-(1-fluoro-2-halo-ethyl)(thiono)phosphoric(phosphonic) acid ester-amides of the formula

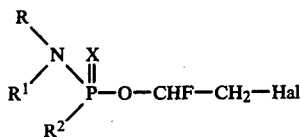   (I)

in which

R and R¹ independently represent hydrogen, alkyl, haloalkyl or cyanoalkyl, or

R and R¹ conjointly with the nitrogen atom form a heterocyclic ring which can optionally be interrupted by further hetero-atoms, R² represents

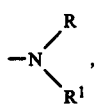

alkoxy, halogenalkoxy or alkyl, Hal represents chlorine or bromine and

X represents oxygen or sulphur.

Preferably R and R¹ independently represent hydrogen or straight-chain or branched alkyl with 1 to 4 carbon atoms, or R and R¹ conjointly with the nitrogen atom represent a 6-membered heterocyclic ring which is optionally interrupted by oxygen, R² represents

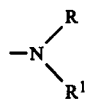

having the above meaning, or straight-chain or branched alkyl, alkoxy or halogenalkoxy in each case with 1 to 3 carbon atoms, and Hal represents chlorine or bromine.

If R and/or R¹ is/are alkyl, a carbon atom content of 1 to 3 is especially preferred. If R and R¹ and the nitrogen form a heterocyclic ring, this may for example be a piperidine or morpholine radical.

Surprisingly, the O-(1-fluoro-2-halo-ethyl)(thiono)-phosphoric(phosphonic) acid ester-amides according to the invention exhibit a better insecticidal, acaricidal and nematocidal action than the corresponding chlorine-substituted alkylphosphoric(phosphonic) acid esters of analogous structure and of the same type of action. The products according to the present invention thus represent a genuine enrichment of the art.

The invention also provides a process for the production of an O-(1-fluoro-2-halo-ethyl)(thiono)phosphoric(phosphonic) acid ester-amide of the formula (I) in which (a) in the case where R² represents alkyl, an O-(1-fluoro-2-halo-ethyl)(thiono)-phosphonic acid ester halide of the formula

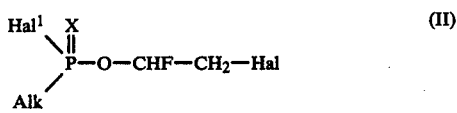   (II)

in which

Hal and X have the above-mentioned meanings,

Alk represents alkyl and

Hal¹ represents halogen, preferably chlorine, is reacted with an amine of the formula

   (III)

in which

R and R¹ have the above-mentioned meanings, optionally in the presence of an acid acceptor and optionally in the presence of a solvent, or (b) in the case where R² represents

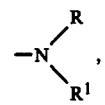

an O-(1-fluoro-2-halo-ethyl)(thiono)-phosphoric acid ester dihalide of the formula

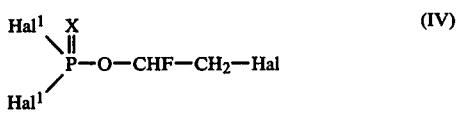   (IV)

in which

X, Hal and Hal¹ have the above-mentioned meanings, is reacted with an amine of the formula (III), optionally in the presence of an acid acceptor and optionally in the presence of a solvent, or (c) in the case where R² represents alkoxy or halogenalkoxy, an O-alkyl-O-(1-fluoro-2-halo-ethyl(thiono)-phosphoric acid diester halide of the formula

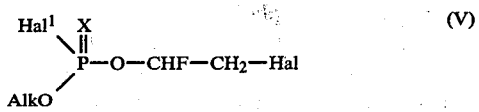

in which

Hal, Hal¹ and X have the above-mentioned meanings, and

Alk represents alkyl or halogenalkyl, is reacted with an amine of the formula (III), optionally in the presence of an acid acceptor and optionally in the presence of a solvent, or (d) in the case where $R^2$ represents alkoxy or halogenalkoxy and X represents oxygen, an O-(1-fluoro-2-halo-ethyl)-phosphoric acid ester dihalide of the formula

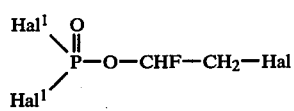

in which

Hal and Hal¹ have the above-mentioned meanings, is first reacted with an amine of the formula (III) and subsequently with an alcohol of the formula AlkOH       (VII)

in which

Alk has the above-mentioned meaning, optionally in the form of an alkali metal salt or alkaline earth metal salt or, in the presence of an acid acceptor and optionally in the presence of a solvent.

Preferably, Alk represents straight-chain or branched alkyl with 1 to 3 carbon atoms.

If, for example, O-(1-fluoro-2-chloro-ethyl)-thionoethanephosphonic acid ester chloride and diethylamine, or O-(1-fluoro-2-chloro-ethyl)-thiono-phosphoric acid ester dichloride and moropholine or O-methyl-O-(1-fluoro-2-chloroethyl)-phosphoric acid diester chloride and methylamine or O-(1-fluoro-2-chloro-ethyl)-phosphoric acid ester dichloride, methylamine and ethanol are used as starting materials, the course of the reaction can be represented by the following formula schemes:

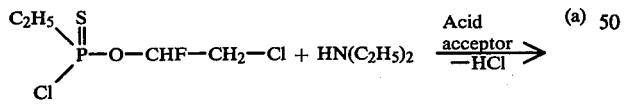

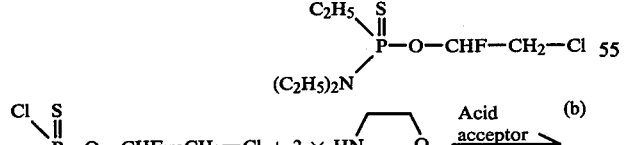

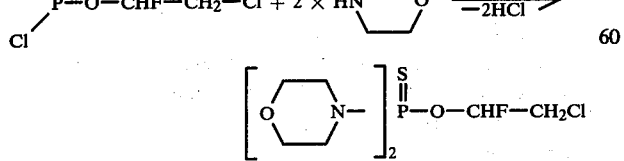

-continued

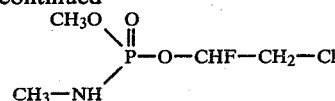

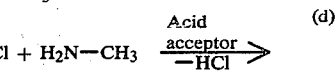

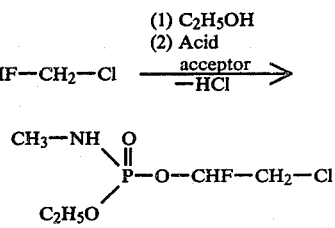

The formulae (II) to (VII) provide a general definition of the starting materials to be used.

The amines (III) and alcohols (VII) are known and can be prepared on an industrial scale in accordance with customary processes. The following may be mentioned as individual examples: ammonia, dimethylamine, diethylamine, di-n-propylamine, di-isopropylamine, N-methyl-propylamine, piperidine and morpholine, and also monomethylamine, monoethylamine, mono-n-propylamine, or mono-iso-propylamine and n-butylamine, sec.-butylamine, tert.-butylamine and iso-butylamine, 1-chloro-2-aminopropane, N-cyanoethylmethylamine, as well as methanol, ethanol and n- and isopropanol, 2-chloroethanol, 1-chloropropanol-2.

The O-(1-fluoro-2-halo-ethyl)-phosphonic acid ester halides, O-(1-fluoro-2-halo-ethyl)-phosphoric acid ester dihalides and O-alkyl-O-(1-fluoro-2-halo-ethyl)-phosphoric acid diester halides are new and can be prepared in accordance with a new process by reacting a phosphoric(phosphonic) acid ester and vinyl fluoride, with simultaneous use of halogenating agents, such as chlorine or bromine, at temperatures between $-50°$ C. and $+120°$ C., if appropriate in the presence of a Friedel-Crafts catalyst and, if appropriate, in the presence of a solvent, to give the corresponding O-(1-fluoro-2-haloethyl)-phosphoric(phosphonic) acid ester halides in accordance with the following formula scheme:

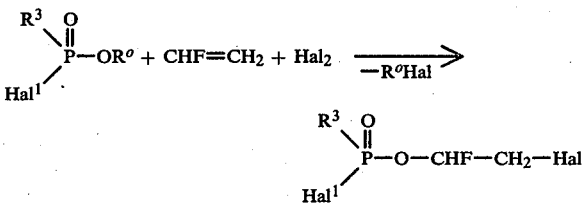

wherein

Hal and Hal¹ have the above-mentioned meanings, $R^3$ represents alkyl, alkoxy or Hal¹, and $R^0$ represents alkyl.

The following may be mentioned as individual examples of the O-(1-fluoro-2-halo-ethyl)-phosphonic acid ester halides, O-(1-fluoro-2-halo-ethyl)-phosphoric acid ester halides and O-alkyl-O-(1-fluoro-2-halo-ethyl)-alkylphosphoric acid diester halides: methane-, ethane-, n-propane- and iso-propane-O-(2-chloro-1-fluoroethyl)-phosphonic acid ester chloride, O-(2-chloro-1-fluoro-ethyl)-phosphoric acid ester dichloride, O-(2- bromo-1-fluoro-ethyl)-phosphoric acid diester chloride, O-methyl-, O-ethyl-, O-n-propyl- and O-iso-propyl-O-(2-chloro-1-fluoro-ethyl)-phosphoric acid diester chloride, and O-methyl-, and O-ethyl-(2-bromo-1-fluoro-ethyl)-phosphoric acid diester chloride.

The O-(1-fluoro-2-halogeno-ethyl)-thionophosphoric acid ester dihalides and -thionophosphonic acid ester monohalides can be obtained from the corresponding

compounds by reaction with alkane- or aryl-dithiophosphonic acid anhydrides, if appropriate mixed with phosphorus sulphochloride and, if appropriate, in the presence of a solvent, in accordance with the following formula scheme:

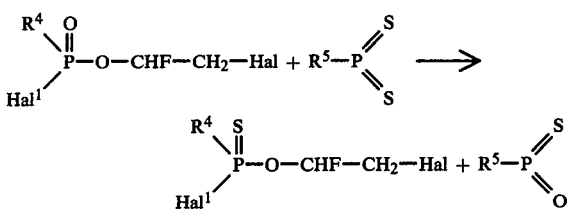

wherein
Hal and Hal¹ have the above-mentioned meanings,
R⁴ represents Hal¹ or alkyl and
R⁵ represents alkyl or aryl.

The following may be mentioned as individual examples of the O-(1-fluoro-2-chloro-ethyl)-thionophosphoric acid ester dihalides and -thionophosphonic acid ester monohalides: methane-, ethane-, n-propane- and iso-propane-O-(2-chloro-1-fluoro-ethyl)-thionophosphonic acid ester chloride and O-(2-chloro-1-fluoro-ethyl)-thionophosphoric acid ester dichloride.

The O-(1-fluoro-2-halo-ethyl)-O-alkyl-thionophosphoric acid diester halides are new but can be prepared from the O-(1-fluoro-2-halo-ethyl)-thionophosphoric acid ester dihalides by reaction with alcohols, in accordance with processes of a type which is known from the literature. The following may be mentioned as individual examples: O-methyl-, O-ethyl-, O-n-propyl- and O-iso-propyl-O-(2-chloro-1-fluoro-ethyl)-thionophosphoric acid diester chloride.

The process for the preparation of the compounds according to the invention is preferably carrier out in the presence of a solvent, which term includes a mere diluent. Virtually all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; nitriles, for example acetonitrile and propionitrile.

All customary acid-binding agents can be used as acid acceptors. Alkali metal carbonates, such as sodium carbonate and potassium carbonate, have proved particularly suitable, as have aliphatic, aromatic or heterocyclic amines, for example triethylamine, trimethylamine, dimethylaniline, dimethylbenzylamine and pyridine. Alternatively, an excess of the particular amine to be employed in the reaction can in each case serve as an acid acceptor.

The reaction temperature can be varied within a substantial range. In general, the reaction is carried out at 0° to 100° C., preferably at 20° to 40° C.

In general, the reaction is allowed to take place under normal pressure.

To carry out process variant (a), the reactants are preferably employed in equimolar ratio. An excess of one or other component produces no essential advantages. The reaction is preferably carried out in one of the stated solvents, in the presence of an acid acceptor. The batch is worked up in accordance with customary methods by filtration, washing the filtrate and distilling off the solvent.

In process variant (b), the phosphoric acid ester dihalide (IV) is employed in a molar ratio of 1:2 to the amine, and in other respects the procedure described above may be followed.

In process variants (c) and (d), the reactants are again generally employed in equimolar ratio and working up may take place as indicated above.

Several of the new compounds (I) are obtained in a crystalline form and are characterized by their sharp melting points. Others are liquids with constant boiling points. Some are obtained in the form of oils which cannot be distilled without decomposition, but can be freed from the last volatile constituents by so-called "slight distillation", that is to say prolonged heating under reduced pressure at moderately elevated temperatures, and they can be purified in this way. They are characterized by the refractive index.

As already mentioned, the O-(1-fluoro-2-halo-ethyl)(thiono)-phosphoric(phosphonic) acid ester-amides according to the invention are distinguished by an excellent insecticidal, acaricidal and nematocidal activity. They are active against plant pests, hygiene pests and pests of stored products and possess a relatively low phytotoxicity and a good action against both sucking and biting insects and mites.

For this reason, the compounds according to the invention can be employed successfully as pesticides in plant protection as well as in the hygiene field and the field of protection of stored products.

The active compounds are well tolerated by plants, have a favorable level of toxicity to warm-blooded animals, and can be used for combating animal pests, especially insects and arachnida and nematodes which are encountered in agriculture, in forestry, in the protection of stored products and of materials, and in the hygiene field. They are active against normally sensitive and resistant species and against all or some stages of development. The above-mentioned pests include:

From the order of the Isopoda, for example *Oniscus asellus, Armadillidium vulgare* and *Porcellio scaber.* From the order of the Diplopoda, for example *Blaniulus guttulatus.* From the order of the Chilopoda, for example *Geophilus carpophagus* and *Scutigera* spec. From the order of the Symphyla, for example *Scutigerella immaculata.* From the order of the Thysanura, for example *Lepisma saccharina.* From the order of the Collembola, for example *Onychiurus armatus.* From the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example *Forficula auricularia.* From the order of the Isoptera, for example Reticulitermes spp. From the order of the Anoplura, for example *Phylloxera vastatrix*, Pemphigus spp., *Pediculus humanus corporis*, Haematopinus spp. and Linognathus spp. From the order of the Mallophaga, for example Trichodectes spp. and Damalinea spp. From the order of the Thysanoptera, for example *Hercinothrips femoralis* and *Thrips tabaci*. From the order of the Heteroptera, for example Eurygaster spp., *Dysdercus intermedius, Piesma quadrata, Cimex lectularius, Rhodnius prolixus* and Triatoma spp. From the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia olea, Laodelphax striatellus, Nilaparvata lugens, Aonidiella aurantii, Aspidiotus hederae,* Pseudococcus spp. and Psylla spp.. From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana.* From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Phylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp, *Melolontha melolontha, Amphimallon solstitialis* and *Costelytra zealandica.* From the order of the Hymenoptera, for example Diprion spp., Hoplocampa spp., Lasius spp., *Monomorium pharaonis* and Vespa spp. From the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp. Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example *Xenopsylla cheopis* and Ceratophyllus spp.. From the order of the Arachnida, for example *Scorpio maurus* and *Latrodectus mactans.* From the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.. The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides, acaricides and nematocides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against neamtodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aformentioned concentration ranges.

The unexpected superiority and outstanding activity of the particular new compounds of the present invention are illustrated, without limitation, by the following examples:

EXAMPLE 1

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil, given in ppm (=mg/l) was decisive. The soil was filled into pots and the pots were left to stand at room temperature.

After 24 hours, the test insects were introduced into the treated soil and after a further 2 to 7 days the degree of effectiveness of the active compound was determined in % by counting the dead and live test insects. The degree of destruction was 100% if all test insects had been killed and was 0% if just as many test insects were still alive as in the case of the control.

The active compounds, the amounts used and the results can be seen from Table 1.

Table 1

*Tenebrio molitor* larvae in the soil

| Active compound | Degree of destruction in % at an active compound concentration of 20 ppm |
|---|---|
| $Cl-CH_2-CH(Cl)-O-P(=O)(OC_2H_5)_2$ <br> (known) (A) | 0 |
| $C_2H_5-P(=O)(NH_2)(O-CHF-CH_2Cl)$ <br> (14) | 100 |
| $CH_3-CH_2-CH_2-O-P(=O)(NHC_3H_7\text{-iso})(O-CHF-CH_2-Cl)$ <br> (10) | 100 |
| $CH_3-CH_2-CH_2-CH_2-O-P(=O)(NHC_3H_7\text{-iso})(O-CHF-CH_2-Cl)$ <br> (9) | 100 |

EXAMPLE 2

Root-systemic action
Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrated was diluted with water to the desired concentration.

The preparation of active compound was intimately mixed with the soil. The concentration of the active compound in the preparation was of practically no importance; only the amount of active compound per unit volume of soil, given in ppm (=mg/l) was decisive.

The treated soil was filled into pots and these were planted with cabbage (*Brassica oleracea*). The active compound could in this way be taken up from the soil by the plant roots and could be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all test insects had been killed and 0% when just as many test insects were still alive as in the case of the untreated control.

The active compounds, the amounts used and the results can be seen from Table 2.

Table 2

Root systemic action (*Phaedon cohleariae* larvae)

| Active compound | Degree of destruction in % at an active compound concentration of 20 ppm |
|---|---|
| $Cl-CH_2-CH(Cl)-O-P(=O)(OC_2H_5)_2$ <br> (known) (A) | 0 |
| $C_2H_5O-P(=O)(NH-C_3H_7\text{-iso})(O-CH(F)-CH_2-Cl)$ <br> (2) | 100 |
| $C_2H_5O-P(=O)(N(C_2H_5)_2)(O-CH(F)-CH_2-Cl)$ <br> (5) | 100 |
| $C_2H_5-P(=O)(NH_2)(O-CH(F)-CH_2-Cl)$ <br> (14) | 100 |

Table 2-continued

Root systemic action (*Phaedon cohleariae* larvae)

| Active compound | Degree of destruction in % at an active compound concentration of 20 ppm |
|---|---|
| CH₃—CH₂—CH₂—O—P(=O)(O—CHF—CH₂—Cl)(NHC₃H₇-iso)  (10) | 100 |
| CH₃—CH₂—CH₂—CH₂—O—P(=O)(OCHF—CH₂—Cl)(NHC₃H₇-iso)  (9) | 100 |
| (CH₃)(C₂H₅)CH—O—P(=O)(O—CHF—CH₂—Cl)(NHC₃H₇-iso)  (8) | 100 |
| Cl—CH₂—CHF—O—P(=S)(OCH₃)(NH₂)  (3) | 100 |

EXAMPLE 3

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrated was diluted with water to the desired concentration.

The preparation of active compound was intimately mixed with soil which was heavily infested with the test nematodes. The concentration of the active compound in the preparation was of practically no importance; only the amount of active compounds per unit volume of soil, given in ppm, was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from Table 3:

Table 3

Nematodes (*Meloidogyne incognita*)

| Active compound | Degree of destruction in % at an active compound concentration of 20 ppm |
|---|---|
| Cl—CH₂—CHCl—O—P(=O)(OC₂H₅)(OC₂H₅)  (known) (A) | 0 |
| C₂H₅O—P(=O)(O—CHF—CH₂—Cl)(NHC₃H₇-iso)  (2) | 100 |
| C₂H₅O—P(=O)(O—CHF—CH₂—Cl)(N(C₂H₅)₂)  (5) | 100 |
| C₂H₅—P(=O)(O—CHF—CH₂Cl)(NH₂)  (14) | 100 |

Table 3-continued

Nematodes (*Meloidogyne incognita*)

| Active compound | Degree of destruction in % at an active compound concentration of 20 ppm |
|---|---|
| 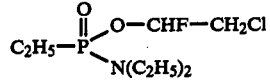 (15) | 100 |
| 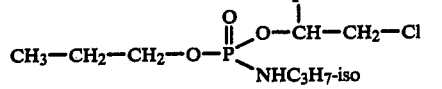 (10) | 100 |
| 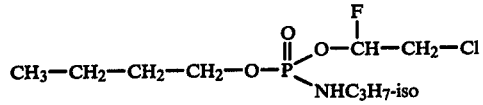 (9) | 100 |
| 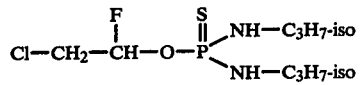 (17) | 100 |
| 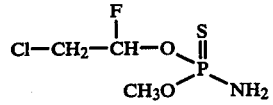 (3) | 100 |

EXAMPLE 4

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrated was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from Table 4.

Table 4

| Active compound | (Myzus Test) Active compound concentration in % by weight | Degree of destruction in 5% after 1 day |
|---|---|---|
| $(CH_3O)_2\overset{O}{\overset{\|}{P}}-\underset{OH}{\overset{\|}{CH}}-CCl_3$ (known) (B) | 0.1<br>0.01 | 50<br>0 |
| $CH_3O-\overset{S}{\overset{\|}{P}}\underset{NH_2}{\overset{OCHF-CH_2-Cl}{\diagup}}$ (3) | 0.1<br>0.01 | 10<br>100<br>100 |
| $C_2H_5-\overset{O}{\overset{\|}{P}}\underset{NH_2}{\overset{OCHF-CH_2-Cl}{\diagup}}$ (14) | 0.1<br>0.01 | 100<br>90 |
| $C_2H_5O-\overset{O}{\overset{\|}{P}}\underset{NH-C_3H_7\text{-iso}}{\overset{OCHF-CH_2-Cl}{\diagup}}$ (2) | 0.1<br>0.01 | 100<br>100<br>20 |
| $\underset{C_2H_5}{\overset{CH_3}{\diagdown}}CH-O-\overset{O}{\overset{\|}{P}}\underset{NH-C_3H_7\text{-iso}}{\overset{OCHF-CH_2-Cl}{\diagup}}$ (8) | 0.1<br>0.01 | 100<br>70<br>25 |
| $n\text{-}C_3H_7-O-\overset{O}{\overset{\|}{P}}\underset{NH-C_3H_7\text{-iso}}{\overset{OCHF-CH_2-Cl}{\diagup}}$ (10) | 0.1<br>0.01 | 100<br>100 |
| $n\text{-}C_4H_9-O-\overset{O}{\overset{\|}{P}}\underset{NH-C_3H_7\text{-iso}}{\overset{OCHF-CH_2-Cl}{\diagup}}$ (9) | 0.1<br>0.01 | 30<br>100<br>100 |
| $C_2H_5O-\overset{O}{\overset{\|}{P}}\underset{N(CH_3)_2}{\overset{OCHF-CH_2-Cl}{\diagup}}$ (6) | 0.1<br>0.01 | 100<br>35 |
| $C_2H_5O-\overset{O}{\overset{\|}{P}}\underset{N(C_2H_5)_2}{\overset{OCHF-CH_2-Cl}{\diagup}}$ (5) | 0.1<br>0.01 | 100<br>99 |
| $C_2H_5-\overset{O}{\overset{\|}{P}}\underset{\text{morpholino}}{\overset{OCHF-CH_2-Cl}{\diagup}}$ (13) | 0.1<br>0.01 | 100<br>100 |
| $C_2H_5O-\overset{O}{\overset{\|}{P}}\underset{\text{morpholino}}{\overset{OCHF-CH_2-Cl}{\diagup}}$ (12) | 0.1<br>0.01 | 100<br>70<br>50 |

EXAMPLE 5

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the common or two-spotted spider mite (*Tetranychus urticae*) in all stages of development were sprayed with the preparation of the active compound until dripping wet.

After the specified periods of time, the degree of destruction was determined as a percentage: 100% means that all the spiter mites were killed whereas 0% means that none of the spider mites were killed.

The active compounds, the concentrations of the active compounds, the evaluation times and the results can be seen from Table 5.

Table 5

(Tetranychus test)

| Active compound | Active Compound concentration in % by weight | Degree of destruction in % after 2 days |
|---|---|---|
| $(CH_3O)_2\overset{O}{\overset{\|}{P}}-\underset{OH}{\overset{}{C}H}-CCl_3$ (known) (B) | 0.1 | 0 |
| $CH_3O-\overset{S}{\overset{\|}{P}}\overset{OCHF-CH_2-Cl}{\diagdown NH_2}$ (3) | 0.1 | 98 |
| $C_2H_5O-\overset{O}{\overset{\|}{P}}\overset{OCHF-CH_2-Cl}{\diagdown NH-C_3H_7-iso}$ (2) | 0.1 | 80 |

EXAMPLE 6

LT$_{100}$ test for Diptera
Test animals: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from Table 6.

Table 6

(LT$_{100}$ test for *Diptera/Musca domestica*)

| Active compound | Active compound concentrations % strength solution by weight | LT$_{100}$ in hours (hrs) |
|---|---|---|
| $Cl_3-\underset{OH}{\overset{}{C}H}-\overset{O}{\overset{\|}{P}}-(OCH_3)_2$ (known) (B) | 0.002 | 6 = 0 |
| 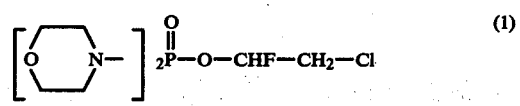 (3) | 0.002 | 6 |
| $Cl-CH_2CH-O-\overset{O}{\overset{\|}{P}}\overset{C_2H_5}{\diagdown NH_2}$ with F on CH (14) | 0.002 | 6 |

Table 6-continued

(LT$_{100}$ test for *Diptera/Musca domestica*)

| Active compound | Active compound concentrations % strength solution by weight | LT$_{100}$ in hours (hrs) |
|---|---|---|
| $Cl-CH_2-\underset{F}{\overset{}{C}H}-O-\overset{O}{\overset{\|}{P}}\overset{OC_2H_5}{\diagdown N(C_2H_5)_2}$ (5) | 0.002 | 6 |
| 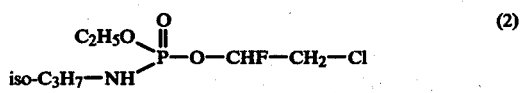 (2) | 0.002 | 6 |

The following further examples are set forth to illustrate, without limitation, the manner of producing the instant compounds according to the present invention:

EXAMPLE 7

$$\left[\begin{array}{c}\diagup\!\!\diagdown\\O\phantom{xx}N-\\\diagdown\!\!\diagup\end{array}\right]_2\overset{O}{\overset{\|}{P}}-O-CHF-CH_2-Cl \quad (1)$$

35 g (0.4 mol) of morpholine were added to a solution of 22 g (0.1 mol) of O-(1-fluoro-2-chloro-ethyl)-phosphoric acid ester dichloride in 250 ml of benzene at 20° to 25° C., the reaction mixture was stirred for a further 3 hours, the morpholine hydrochloride which had separated out was filtered off, the mother liquor was concentrated and the residue was recrystallized from a mixture of ethyl acetate and ligroin. 22 g (70% of theory) of O-(1-fluoro-2-chloro-ethyl)-phosphoric acid ester dimorpholide of melting point 90°-92° C. were thus obtained.

EXAMPLE 8

$$\underset{iso-C_3H_7-NH}{\overset{C_2H_5O}{\diagdown}}\overset{O}{\overset{\|}{P}}-O-CHF-CH_2-Cl \quad (2)$$

23.6 g of iso-propylamine, dissolved in 30 ml of ether, were added dropwise in the course of 2 hours to a solution of 43.1 g of 0-(1-fluoro-2-chloro-ethyl)-phosphoric acid ester dichloride in 100 ml of diethyl ether while stirring, and cooling externally at 20° to 30° C. After 20 hours, the isopropylamine hydrochloride which had precipitated (20 g) was filtered off, the ether solution of the O-(1-fluoro-2-chloro-ethyl)-N-iso-propylphosphoric acid ester-amide chloride thus obtained was treated dropwise, while stirring and cooling, with a solution of 9.5 g of ethanol and 22 g of triethylamine in 200 ml of diethyl ether, the reaction mixture was stirred at room temperature after 10 hours, and thereafter the triethylamine hydrochloride which had precipitated was filtered off and the ether was distilled off under normal pressure. The reaction product was separated from high-boiling by-products by distillation in a thin film evaporator at 150° C. under a pressure of 0.3 mm Hg. 35 g (70%) of theory of O-ethyl-O-1-(fluoro-2- chloro-ethyl)-N-isopropylphosphoric acid ester-amide of boiling point 131/133° C./0.5 mm Hg were obtained.

EXAMPLE 9

(a) 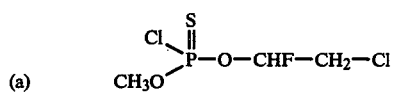

0.2 mol of a sodium methylate solution was added, while cooling, to a solution of 47 g (0.2 mol) of O-(1-fluoro-2-chloro-ethyl)-thionophosporic acid ester dichloride in 300 ml of toluene, the mixture was further stirred for 30 minutes at a temperature of 10° C. and was washed twice with water, the organic layer was dried over sodium sulphate, the toluene was evaporated off under reduced pressure and the residue was distilled. O-Methyl-O-(1-fluoro-2-chloro-ethyl)-thionophosphoric acid diester chloride of boiling point 38°–42° C./0.01 mm Hg was obtained in 81% yield.

(b) 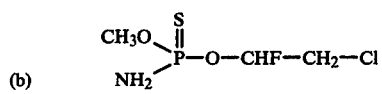 (3)

Ammonia was passed into a solution of 23 g (0.1 mol) of O-methyl-O-(1-fluoro-2-chloro-ethyl)-thionophosphoric acid diester chloride in 200 ml of acetonitrile at +20° C., until the reaction had ended. The reaction mixture was poured into water and was taken up in toluene, the organic phase was washed with water and dried over sodium sulphate, the toluene was evaporated off and the residue was distilled off under greatly reduced pressure. 16 g (77% of theory) of O-methyl-O-(1-fluoro-chloro-ethyl)-thionophosphoric acid diester-amide of refractive index $n_D^{23}$: 1.4930 were obtained.

EXAMPLE 10

(a) 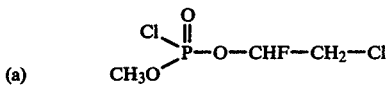

55 g of vinyl fluoride and 70 g of chlorine were passed simultaneously into 308 g of O,O-dimethylphosphoric acid diester chloride at −5° C. to 0° C., while stirring and cooling. After completion of the reaction, the mixture was first degassed at room temperature under reduced pressure and was then fractionally distilled. 143 g (69% of theory) of O-methyl-O-(1-fluoro-2-chloro-ethyl)-phosphoric acid diester chloride of boiling point 69°–72° C./0.03 mm Hg were obtained.

(b) 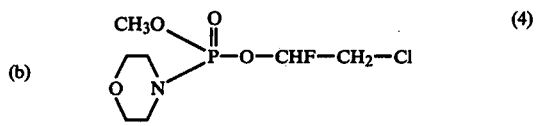 (4)

8.7 g (0.1 mol) of morpholine were added, at a temperature of 20° to 25° C., to a solution of 11 g (0.05 mol) of O-methyl-O-(1-fluoro-2-chloro-ethyl)-phosphoric acid diester chloride in 200 ml of benzene. The reaction mixture was stirred for a further 4 hours, the morpholine hydrochloride which had precipitated was filtered off, the solvent was evaporated off in vacuo and the residue was subjected to slight distillation under greatly reduced pressure. This gave 11 g (84% of theory) of O-methyl-O-(1-fluoro-2-chloro-ethyl)-phosphoric acid diester morpholine of refractive index $n_D^{22}$: 1.4599.

EXAMPLE 11

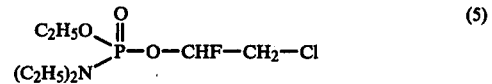 (5)

A solution of 15 g of diethylamine in 30 ml of ether was added dropwise to a solution of 22.5 g of O-ethyl-O-(1-fluoro-2-chloro-ethyl)-phosphoric acid diester monochloride (prepared, as described under Example 10(a), from O,O-diethyl-phosphoric acid diester chloride and chlorine) in 30 ml of diethyl ether, while cooling and stirring the reaction mixture at 20° to 30° C.; after 6 hours the diethylamine hydrochloride which had precipitated was filtered off, the precipitate was washed with ether and after distilling off the ether under normal pressure the resulting crude product was purified by vacuum distillation. 25 g (95% of theory) of O-ethyl-O-(1-fluoro-2-chloro-ethyl)-N,N-diethyl-phosphoric acid diester-amide of boiling point 103° to 105° C./0.5 mm Hg were obtained.

The following compounds were obtained analogously to Examples 7 to 11:

Table 7

| Compound No. | Active compound | Physical data |
|---|---|---|
| 6 | $C_2H_5O$, $(CH_3)_2N$ — P(=O) — O—CHF—CH$_2$—Cl | Boiling point 92° C./ 0.5 mm Hg |
| 7 | $C_2H_5O$, piperidino — P(=O) — O—CHF—CH$_2$—Cl | Melting point 150° |
| 8 | iso-$C_3H_7$—NH, sec.-$C_4H_9O$ — P(=O) — O—CHF—CH$_2$—Cl | $n_D^{20}$: 1.4385 |
| 9 | iso-$C_3H_7$—NH, n-$C_4H_9O$ — P(=O) — O—CHF—CH$_2$—Cl | $n_D^{20}$: 1.4395 |

Table 7-continued

| Compound No. | Active compound | Physical data |
|---|---|---|
| 10 | iso-C$_3$H$_7$—NH\\P(=O)(n-C$_3$H$_7$O)—O—CHF—CH$_2$—Cl | n$_D^{20}$ :1.4428 |
| 11 | iso-C$_3$H$_7$—NH\\P(=O)(iso-C$_3$H$_7$O)—O—CHF—CH$_2$—Cl | n$_D^{20}$ :1.4430 |
| 12 | morpholino\\P(=O)(C$_2$H$_5$O)—O—CHF—CH$_2$—Cl | n$_D^{20}$ :1.4550 |
| 13 | morpholino\\P(=O)(C$_2$H$_5$)—O—CHF—CH$_2$—Cl | Boiling point 125–30° C./0.5 mm Hg |
| 14 | C$_2$H$_5$\\P(=O)(H$_2$N)—O—CHF—CH$_2$—Cl | Melting point 180° |
| 15 | (C$_2$H$_5$)$_2$N\\P(=O)(C$_2$H$_5$)—O—CHF—CH$_2$—Cl | Boiling point 100° C./0.4 mm Hg |
| 16 | [(CH$_3$)$_2$N]$_2$P(=O)—O—CHF—CH$_2$—Cl | Boiling point 84°–87° C./0.1 mm Hg |
| 17 | (iso-C$_3$H$_7$—NH)$_2$P(=O)—O—CHF—CH$_2$—Cl | n$_D^{24}$ :1.4908 |
| 18 | (C$_2$H$_5$)$_2$N\\P(=O)(CH$_3$O)—O—CHF—CH$_2$—Cl | n$_D^{20}$ :1.4345 |
| 19 | C$_2$H$_5$—NH—P(=O)(OCH$_3$)—O—CHF—CH$_2$Cl | n$_D^{20}$ :1.4383 |
| 20 | C$_2$H$_5$—NH—P(=O)(OC$_2$H$_5$)—O—CHF—CH$_2$Cl | |
| 21 | C$_2$H$_5$O—P(=O)(HNC$_4$H$_9$n)—O—CHF—CH$_2$Cl | |
| 22 | C$_2$H$_5$—O—P(=O)(NH—CH$_3$)—O—CHF—CH$_2$Cl | n$_D^{20}$ :1.4358 |
| 23 | C$_2$H$_5$—O—P(=O)(NH—CH(CH$_3$)—C$_2$H$_5$)—O—CHF—CH$_2$Cl | n$_D^{20}$ :1.4371 |
| 24 | C$_2$H$_5$O\\P(=O)(nC$_3$H$_7$NH)—O—CHF—CH$_2$Cl | |
| 25 | CH$_3$O\\P(=O)((C$_2$H$_5$)$_2$N)—O—CHF—CH$_2$Br | n$_D^{20}$ = 1.4500 |
| 26 | C$_2$H$_5$O\\P(=O)(C$_2$H$_5$NH)—O—CHF—CH$_2$Br | n$_D^{20}$ = 1.4501 |
| 27 | C$_2$H$_5$O\\P(=O)(C$_2$H$_5$—CH(CH$_3$)—NH)—O—CHF—CH$_2$Br | n$_D^{20}$ = 1.4499 |

Table 7-continued

| Compound No. | Active compound | Physical data |
|---|---|---|
| 28 | (CH₃O)(C₂H₅NH)P(O)—O—CHF—CH₂Br | |
| 29 | (CH₃O)(C₂H₅CH(CH₃)NH)P(O)—O—CHF—CH₂Br | |
| 30 | (CH₃O)(C₂H₅N(CH₃))P(O)—O—CHF—CH₂Br | |
| 31 | (C₂H₅O)(C₂H₅N(CH₃))P(O)—O—CHF—CH₂Br | |
| 32 | (CH₃O)(C₂H₅N(CH₃))P(O)—O—CHF—CH₂Cl | |
| 33 | (C₂H₅O)(C₂H₅N(CH₃))P(O)—O—CHF—CH₂Cl | |
| 34 | (n-C₃H₇O)(C₂H₅N(CH₃))P(O)—O—CHF—CH₂Cl | |
| 35 | (n-C₃H₇O)(C₂H₅N(CH₃))P(O)—O—CHF—CH₂Br | |
| 36 | (n-C₃H₇O)(C₂H₅CH(CH₃)NH)P(O)—O—CHF—CH₂Br | |
| 37 | (n-C₃H₇O)(C₂H₅CH(CH₃)NH)P(O)—O—CHF—CH₂Cl | |
| 38 | (i-C₃H₇O)(C₂H₅CH(CH₃)NH)P(O)—O—CHF—CH₂Br | |
| 39 | (i-C₃H₇O)(C₂H₅CH(CH₃)NH)P(O)—O—CHF—CH₂Cl | |
| 40 | (CH₃O)(ClCH₂—CH₂—NH)P(O)—O—CHF—CH₂Cl | |
| 41 | (CH₃O)(ClCH₂—CH₂—NH)P(O)—O—CHF—CH₂Br | |

Table 7-continued

| Compound No. | Active compound | Physical data |
|---|---|---|
| 42 | (C$_2$H$_5$O)(ClCH$_2$—CH$_2$HN)P(O)—O—CHF—CH$_2$Cl | |
| 43 | (C$_2$H$_5$O)(ClCH$_2$—CH$_2$HN)P(O)—O—CHF—CH$_2$Br | |
| 44 | (CH$_3$O)(ClCH$_2$—CH(CH$_3$)—HN)P(O)—O—CHF—CH$_2$Cl | |
| 45 | (CH$_3$O)(ClCH$_2$—CH(CH$_3$)—NH)P(O)—O—CHF—CH$_2$Br | |
| 46 | (C$_2$H$_5$O)(ClCH$_2$—CH(CH$_3$)—NH)P(O)—O—CHF—CH$_2$Br | |
| 47 | (C$_2$H$_5$O)(ClCH$_2$—CH(CH$_3$)—NH)P(O)—O—CHF—CH$_2$Cl | |
| 48 | (C$_2$H$_5$O)(NCCH$_2$—CH$_2$—N(CH$_3$))P(O)—O—CHF—CH$_2$Cl | |
| 49 | (ClC$_2$H$_4$O)(CH$_3$—NH)P(O)—O—CHF—CH$_2$Cl | |
| 50 | (ClCH$_2$—CH$_2$O)(CH$_3$—HN)P(O)—O—CHF—CH$_2$Br | |
| 51 | (ClCH$_2$—CH$_2$O)(C$_2$H$_5$—HN)P(O)—O—CHF—CH$_2$Cl | |
| 52 | (ClCH$_2$—CH$_2$O)(C$_2$H$_5$—HN)P(O)—OCHF—CH$_2$Br | |
| 53 | (ClCH$_2$—CH$_2$—O)((C$_2$H$_5$)$_2$N)P(O)—O—CHF—CH$_2$Cl | |
| 54 | (ClCH$_2$—CH$_2$—O)((C$_2$H$_5$)$_2$N)P(O)—O—CHF—CH$_2$Br | |
| 55 | (ClCH$_2$—CH$_2$—O)(C$_2$H$_5$—CH(CH$_3$)—NH)P(O)—O—CHF—CH$_2$Cl | |
| 56 | (ClCH$_2$—CH$_2$O)(C$_2$H$_5$—CH(CH$_3$)—NH)P(O)—O—CHF—CH$_2$Br | |
| 57 | (ClCH$_2$—CH$_2$O)(iC$_3$H$_7$—NH)P(O)—O—CHF—CH$_2$Cl | |

Table 7-continued

| Compound No. | Active compound | Physical data |
|---|---|---|
| 58 | ClCH$_2$—CH$_2$O\\P(=O)—O—CHF—CH$_2$Br; iC$_3$H$_7$—NH | |
| 59 | ClCH$_2$—CH$_2$O\\P(=O)—O—CHF—CH$_2$Br; C$_2$H$_5$—N(CH$_3$) | |
| 60 | ClCH$_2$—CH$_2$O\\P(=O)—O—CHF—CH$_2$—Cl; C$_2$H$_5$—CH(CH$_3$)—NH | |
| 61 | ClCH$_2$—CH$_2$O\\P(=O)—OCHF—CH$_2$—Br; C$_2$H$_5$—CH(CH$_3$)—NH | |
| 62 | ClCH$_2$—CH(CH$_3$)—O\\P(=O)—OCHF—CH$_2$—Cl; CH$_3$—HN | |
| 63 | ClCH$_2$—CH(CH$_3$)—O\\P(=O)—OCHF—CH$_2$—Br; CH$_3$—HN | |
| 64 | ClCH$_2$—CH(CH$_3$)—O\\P(=O)—OCHF—CH$_2$—Cl; C$_2$H$_5$HN | |
| 65 | ClCH$_2$—CH(CH$_3$)—O\\P(=O)—OCHF—CH$_2$—Br; C$_2$H$_5$HN | |
| 66 | ClCH$_2$—CH(CH$_3$)—O\\P(=O)—OCHF—CH$_2$—Cl; (C$_2$H$_5$)$_2$N | |
| 67 | ClCH$_2$—CH(CH$_3$)—O\\P(=O)—OCHF—CH$_2$—Br; (C$_2$H$_5$)$_2$N | |
| 68 | ClCH$_2$—CH(CH$_3$)—O\\P(=O)—OCHF—CH$_2$Cl; C$_2$H$_5$—N(CH$_3$) | |
| 69 | ClCH$_2$—CH(CH$_3$)—O\\P(=O)—OCHF—CH$_2$—Br; C$_2$H$_5$—N(CH$_3$) | |
| 70 | ClCH$_2$—CH$_2$O\\P(=O)—OCHF—CH$_2$Cl; H$_2$N | |
| 71 | ClCH$_2$—CH$_2$O\\P(=O)—OCHF—CH$_2$—Br; H$_2$N | |
| 72 | ClCH$_2$—CH(CH$_3$)—O\\P(=O)—OCHF—CH$_2$Cl; H$_2$N | |

Table 7-continued

| Compound No. | Active compound | Physical data |
|---|---|---|
| 73 | ClCH$_2$—CH(CH$_3$)—O—P(=O)(NH$_2$)—OCHF—CH$_2$—Br | |
| 74 | CH$_3$O—P(=O)(NH$_2$)—OCHF—CH$_2$Cl | |
| 75 | CH$_3$O—P(=O)(NH$_2$)—OCHF—CH$_2$—Br | |
| 76 | C$_2$H$_5$O—P(=O)(NH$_2$)—OCHF—CH$_2$Cl | |
| 77 | C$_2$H$_5$O—P(=O)(NH$_2$)—OCHF—CH$_2$—Br | |
| 78 | n-C$_3$H$_7$O—P(=O)(NH$_2$)—OCHF—CH$_2$Cl | |
| 79 | n-C$_3$H$_7$O—P(=O)(NH$_2$)—OCHF—CH$_2$—Br | |
| 80 | i-C$_3$H$_7$O—P(=O)(NH$_2$)—OCHF—CH$_2$Cl | |
| 81 | i-C$_3$H$_7$O—P(=O)(NH$_2$)—OCHF—CH$_2$—Br | |
| 82 | n-C$_4$H$_9$O—P(=O)(NH$_2$)—OCHF—CH$_2$Cl | |
| 83 | n-C$_4$H$_9$O—P(=O)(NH$_2$)—OCHF—CH$_2$—Br | |
| 84 | C$_2$H$_5$—CH(CH$_3$)—O—P(=O)(NH$_2$)—OCHF—CH$_2$Cl | |
| 85 | C$_2$H$_5$—CH(CH$_3$)—O—P(=O)(NH$_2$)—OCHF—CH$_2$—Br | |
| 86 | n-C$_3$H$_7$O—P(=O)(NHCH$_3$)—OCHF—CH$_2$Cl | |
| 87 | n-C$_3$H$_7$O—P(=O)(NHCH$_3$)—OCHF—CH$_2$—Br | |
| 88 | n-C$_3$H$_7$O—P(=O)(NHC$_2$H$_5$)—OCHF—CH$_2$Cl | |
| 89 | n-C$_3$H$_7$O—P(=O)(NHC$_2$H$_5$)—OCHF—CH$_2$—Br | |
| 90 | n-C$_3$H$_7$O—P(=O)(NH-i-C$_3$H$_7$)—OCHF—CH$_2$Cl | |
| 91 | n-C$_3$H$_7$O—P(=O)(NH-i-C$_3$H$_7$)—OCHF—CH$_2$—Br | |

Table 7-continued

| Compound No. | Active compound | Physical data |
|---|---|---|
| 92 | n-C$_3$H$_7$O\P(=O)(NH-n-C$_3$H$_7$)—OCHF—CH$_2$Cl | |
| 93 | n-C$_3$H$_7$O\P(=O)(NH-n-C$_3$H$_7$)—OCHF—CH$_2$—Br | |
| 94 | C$_2$H$_5$—CH(CH$_3$)—O\P(=O)(NHCH$_3$)—OCHF—CH$_2$Cl | |
| 95 | C$_2$H$_5$—CH(CH$_3$)—O\P(=O)(NHCH$_3$)—OCHF—CH$_2$—Br | |
| 96 | n-C$_4$H$_9$O\P(=O)(NHCH$_3$)—OCHF—CH$_2$Cl | |
| 97 | n-C$_4$H$_9$O\P(=O)(NHCH$_3$)—OCHF—CH$_2$—Br | |
| 98 | n-C$_4$H$_9$O\P(=O)(NHC$_2$H$_5$)—OCHF—CH$_2$Cl | |
| 99 | n-C$_4$H$_9$O\P(=O)(NHC$_2$H$_5$)—OCHF—CH$_2$—Br | |
| 100 | C$_2$H$_5$—CH(CH$_3$)—O\P(=O)(NHC$_2$H$_5$)—OCHF—CH$_2$Cl | |
| 101 | C$_2$H$_5$—CH(CH$_3$)—O\P(=O)(NHC$_2$H$_5$)—OCHF—CH$_2$—Br | |
| 102 | CH$_3$O\P(=O)(N-pyrrolidinyl)—OCHF—CH$_2$Cl | |
| 103 | CH$_3$O\P(=O)(N-pyrrolidinyl)—OCHF—CH$_2$—Br | |
| 104 | C$_2$H$_5$O\P(=O)(N-pyrrolidinyl)—OCHF—CH$_2$Cl | |
| 105 | C$_2$H$_5$O\P(=O)(N-pyrrolidinyl)—OCHF—CH$_2$—Br | |
| 106 | n-C$_3$H$_7$O\P(=O)(N-pyrrolidinyl)—OCHF—CH$_2$Cl | |

Table 7-continued

| Compound No. | Active compound | Physical data |
|---|---|---|
| 107 | 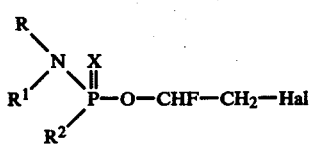 | |
| 108 | | |
| 109 |  | |

It will be appreciated that the instant specification and examples are set forth by way of illustration and not limitation, and that various modifications and changes may be made without departing from the spirit and scope of the present invention.

What is claimed is:

1. An O-(1-fluoro-2-halo-ethyl)(thiono)phosphoric(-phosphonic)acid ester-amide of the formula

in which

R and $R^1$ independently represent hydrogen, alkyl, haloalkyl or cyanoalkyl, or R and $R^1$ conjointly with the nitrogen atom form a piperidine, morpholine or pyrrolidine ring, $R^2$ represents $$-N\begin{matrix}R\\R^1\end{matrix}$$

or alkoxy, halogenalkoxy or alkyl,

Hal represents chlorine or bromine, and

X represents oxygen or sulphur.

2. A method of combating insect, acarid or nematode pests which comprises applying to the pests or a habitat thereof an insecticidally, acaricidally or nematocidally effective amount of a compound according to claim 1.

3. The method according to claim 2 in which said compound is O-ethyl-O-(1-fluoro-2-chloro-ethyl)-N,N-diethyl-phosphoric acid diester-amide, O-n-propyl-O-(1-fluoro-2-chloro-ethyl)-N-isopropyl-phosphoric acid diester-amide, O-methyl-O-(1-fluoro-2-chloro-ethyl)-N-ethyl-phosphoric acid diester-amide, O-ethyl-O-(1-fluoro-2-chloro-ethyl)-N-ethyl-phosphoric acid diester-amide, or O-ethyl-O-(1-fluoro-2-chloro-ethyl)-N-methyl-phosphoric acid diester-amide.

4. A compound according to claim 1 in which R and $R^1$ independently represent hydrogen or straight-chain or branched alkyl with 1 to 4 carbon atoms, or R and $R^1$ conjointly with the nitrogen atom form a piperidine, morpholine or pyrrolidine ring, $R^2$ represents $$-N\begin{matrix}R\\R^1\end{matrix}$$

having the above meaning, or straight-chain or branched alkyl, halogenalkoxy or alkoxy in each case with 1 to 3 carbon atoms, and Hal represents chlorine or bromine.

5. A compound according to claim 1, wherein such compound is O-ethyl-O-(1-fluoro-2-chloro-ethyl)-N,N-diethyl-phosphoric acid diester-amide of the formula

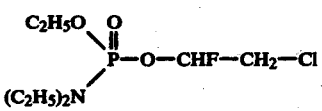

6. A compound according to claim 1, wherein such compound is O-n-propyl-O-(1-fluoro-2-chloro-ethyl)-N-isopropyl-phosphoric acid diester-amide of the formula

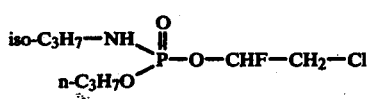

7. A compound according to claim 1, wherein such compound is O-methyl-O-(1-fluoro-2-chloro-ethyl)-N-ethyl-phosphoric acid diester-amide of the formula

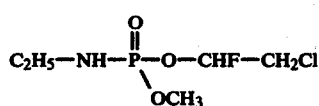

8. A compound according to claim 1, wherein such compound is O-ethyl-O-(1-fluoro-2-chloro-ethyl)-N-ethyl-phosphoric acid diester-amide of the formula

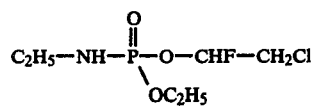
9. A compound according to claim 1, wherein such compound is O-ethyl-O-(1-fluoro-2-chloro-ethyl)-N-methyl-phosphoric acid diester-amide of the formula
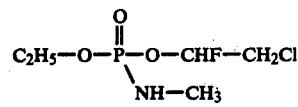
10. An insecticidal, acaricidal or nematocidal composition containing as active ingredient an insecticidally, acaricidally or nematocidally effective amount of a compound according to claim 1 in admixture with a diluent.
* * * * *